(12) United States Patent
Maier et al.

(10) Patent No.: US 6,751,495 B2
(45) Date of Patent: Jun. 15, 2004

(54) METHOD OF FAST AND RELIABLE TISSUE DIFFERENTIATION USING DIFFUSION-WEIGHTED MAGNETIC RESONANCE IMAGING

(75) Inventors: Stephan E. Maier, Brookline, MA (US); Robert V. Mulkern, Jr., Waban, MA (US)

(73) Assignee: Brigham & Womens' Hospital, Boston, MA (US)

( * ) Notice: Subject to any disclaimer, the term of this patent is extended or adjusted under 35 U.S.C. 154(b) by 566 days.

(21) Appl. No.: 09/822,681

(22) Filed: Mar. 30, 2001

(65) Prior Publication Data

US 2001/0039377 A1 Nov. 8, 2001

Related U.S. Application Data

(60) Provisional application No. 60/193,619, filed on Mar. 31, 2000.

(51) Int. Cl.⁷ .............................. A61B 5/05; G01V 3/00
(52) U.S. Cl. ...................................... 600/410; 324/307
(58) Field of Search .......................... 600/410, 411, 600/412, 413, 414, 415, 416, 417, 418, 419, 420, 421, 422, 423; 324/306, 307, 308, 309

(56) References Cited

U.S. PATENT DOCUMENTS

| | | | | | |
|---|---|---|---|---|---|
| 5,327,884 A | * | 7/1994 | Hardy et al. | ............... | 600/411 |
| 5,786,692 A | * | 7/1998 | Maier et al. | ............... | 324/307 |
| 5,899,858 A | * | 5/1999 | Muthupillai et al. | ....... | 600/410 |
| 6,320,378 B1 | * | 11/2001 | Maier et al. | ............... | 324/307 |
| 6,445,184 B1 | * | 9/2002 | Tanttu | .................... | 324/309 |
| 6,501,977 B1 | * | 12/2002 | Kimmlingen | ............. | 600/410 |
| 6,614,225 B1 | * | 9/2003 | Feinberg | ................. | 324/307 |

* cited by examiner

Primary Examiner—Daniel Robinson
(74) Attorney, Agent, or Firm—George W. Neuner; David A. Tucker; Edwards & Angell, LLP

(57) ABSTRACT

Quantified differences, such as $chi^2$ error parameters, between a mono-exponential, logarithmic best fit of a series of line scan diffusion-weighted magnetic resonance signals taken over a range of b-factors between about 100 and about 5000 sec/mm² are obtained. The quantified differences so generated are displayed as an image wherein the brightness of each pixel depends upon the size of its associated quantified difference. The resulting image is characterized by high signal to noise ratio and distinctness between varying tissue types.

5 Claims, 9 Drawing Sheets

| Tissue | $ADC_1$ ($\mu m^2/ms$) | $ADC_2$ ($\mu m^2/ms$) | $A_2/(A_1+A_2)$ |
|---|---|---|---|
| WM    n=15 | 1.25 (0.08) | 0.19 (0.02) | 0.31 (0.04) |
| GM    n=15 | 1.71 (0.12) | 0.37 (0.04) | 0.42 (0.05) |
| Edema n=13 | 1.81 (0.14) | 0.20 (0.05) | 0.10 (0.03) |
| Tumor n=14 | 1.75 (0.20) | 0.23 (0.07) | 0.24 (0.10) |
| Cyst  n= 5 | 2.75 (0.19) | – | – |
| Stroke n= 1 | 0.84 | 0.14 | 0.34 |
| | $A_1/A_1(WM)$ | $A_2/A_2(WM)$ | $\chi^2/\chi^2(WM)$ |
| GM    n=15 | 0.96 (0.10) | 1.55 (0.21) | 0.86 (0.28) |
| Edema n=13 | 2.78 (0.26) | 0.73 (0.25) | 1.88 (0.64) |
| Tumor n=14 | 2.18 (0.57) | 1.53 (0.68) | 4.30 (2.69) |
| Cyst  n= 4 | 4.45 (0.59) | – | 0.19 (0.15) |

Fig. 7

METHOD OF FAST AND RELIABLE TISSUE DIFFERENTIATION USING DIFFUSION-WEIGHTED MAGNETIC RESONANCE IMAGING

This non-provisional application claims priority from United States Provisional Patent Application Serial No. 60/193,619 filed Mar. 31, 2000.

BACKGROUND

1. Field of Invention

The invention generally relates to methods for obtaining, processing and displaying parameters associated with in vivo tissue water diffusion as pathologically significant images using magnetic resonance imaging. More particularly, the invention relates to methods for obtaining and processing diffusion weighted output signals from a magnetic resonance imaging apparatus, and to the fast creation of high definition images of internal bodily tissue(s) utilizing the so processed magnetic resonance output signals.

2. Summary of the Prior Art

Tissue differentiation and localization always have been basic goals of magnetic resonance imaging. Indeed, the desire to distinguish between normal tissue and tumor tissue using magnetic resonance imaging techniques was recognized at least thirty years ago. At that time, it was realized that the spin-lattice, so-called "T1", as well as the spin-spin, so-called "T2", relaxation parameters are different between normal and cancerous tissues. Accordingly, by appropriately mapping the various T1 and/or T2 relaxation times determined from magnetic resonance signals of various voxels in an anatomical slice of interest as relative image amplitudes, it was possible to create images generally showing the demarcation of tumor tissue from adjacent normal tissue.

In the intervening time period, methods of obtaining T1- or T2-weighted images using magnetic resonance imaging techniques have improved. In addition, a large amount of experience has been gained in the in vivo application of these methods in conjunction with the use of various paramagnetic contrast agents. In fact, the latter methodology has evolved to the point that presently the use of contrast agent enhanced T1- and/or T2-weighted imaging for the purpose of demarcating tissue boundaries is considered to be basically conventional. Nevertheless, the determination of tumor margins using this "conventional" methodology still is not entirely successful.

More recently, diffusion-weighted magnetic resonance imaging has been proposed as a novel contrast mechanism for demarcating the boundaries of certain tumors. In this regard, so-called "apparent diffusion coefficient" (ADC) maps seem to provide useful information about the structural details of tumors. Hence, there are reports in the literature that suggest that peritumoral edema, solid enhancing, solid necrotic non-enhancing and cystic parts of tumors can be recognized on ADC maps.

Still further, so-called "diffusion tensor imaging" is believed to add information about the directional dependence of molecular diffusion that may prove to be helpful in the demarcation of tumor margins. Again, however, these methods, even when used in conjunction with contrast enhanced T1 and T2 relaxation-weighted imaging, are not totally successful.

To better understand the above concepts, and the acquisition and use of magnetic resonance measurements of in vivo diffusion as contemplated by the present invention, it will be instructive to first generally discuss some basics. First, the concepts of isotropic diffusion, the so-called "diffusion coefficient", and the measurement of the "diffusion coefficient" with magnetic resonance will be presented in a generalized manner. Second, the concepts of the extension of the definition of diffusion to so-called "anisotropic" diffusion, and the characterization of diffusion with a diffusion tensor, rather than a single coefficient, will be presented. Third, the effects of blood perfusion in the micro-circulatory system as causing deviations in expected magnetic resonance signal behavior will be discussed. Finally, the phenomenon of a departure from the normally adopted magnetic resonance signal behavior when the diffusion encoding range is extended substantially beyond the parameters currently in clinical use will lead to a discussion of the present invention.

First, with regard to isotropic diffusion and its measurement using magnetic resonance, it will be recognized that in a pure liquid such as water at room temperature, the individual water molecules are in constant motion due to the phenomenon of thermal agitation. This phenomenon is commonly referred to as "Brownian motion". The so-called "diffusion coefficient" (herein sometimes referred to as "D") is a measure of this molecular motion, and it can be determined with magnetic resonance techniques.

More particularly, a magnetic field gradient can be used to "tag" atomic level spins in a sample according to their location in space at the time of the application of a first magnetic gradient to the sample. A second gradient, applied at a later time, then serves to probe how far, on average, the individual spins have moved between the time of the first gradient application and the time of the second gradient application. In the ideal case, these magnetic field gradients are applied in brief, strong bursts separated by a common well-defined time period. In practice in clinical magnetic resonance systems, however, the gradients typically are applied for a moderate duration of several tens of milliseconds, and the leading edges of the respective bursts are separated by delays of a similar length of time.

Under these conditions, the diffusion encoding level, i.e., the so-called "b-factor", is defined by the following relationship:

$$b = \gamma^2 G^2 \delta^2 (\Delta - \delta/3)$$

where $\gamma$ is the gyromagnetic ratio (42.58 MHz/Tesla for protons), G is the gradient amplitude, $\delta$ is the duration of each gradient lobe, and $\Delta$ is the separation between lobes. Thus, with one gradient pulse placed prior to and the other following the 180° pulse of a spin echo sequence (90° RF-TE/2–180° RF-TE/2 - acquire), the signal S of the spin-echo measured at echo time TE for isotropic diffusion is given by the mono-exponential relationship:

$$S = S_0 \exp(-bD).$$

In this relationship, $S_0$ depends upon machine constants, the spin-spin relaxation time T2, the spin-lattice relaxation time T1 in any experiment that repeats measurements every repetition time period TR, and the spin density $\rho$. Specifically, the diffusion coefficient D may be measured by making multiple measurements of S as a function of b, plotting the natural logarithm of S vs. b and then performing a linear regression analysis whose slope provides the experimental measurement of D. The value of b is most conveniently varied by keeping the time delay fixed and incrementing the amplitude G of the magnetic field gradient.

As will be seen from FIG. 1, the logarithmic decay of signal intensity from neat solutions of water, ethanol and isopropanol as a function of b derived using a single column sampling technique on a clinical scanner follows a straight-line. This is indicative of mono-exponential decay above the respective baseline noise levels for each of the solutions. The water signal decays the fastest, thereby indicating that it has the highest diffusion coefficient. However, the actual diffusion coefficients measured from the slopes of the decays shown above the base line noise values are in excellent agreement with the published literature for all three samples. Hence, for isotropic diffusion, it may be said that the logarithm of the intensity of the magnetic resonance signal varies linearly with b above a given noise threshold.

Second, the extension of the foregoing concepts to the measurement of tissue water diffusion within the context of magnetic resonance imaging led to certain adjustments in the above-stated theory. Thus, it was quickly realized that in certain organs like the brain, preferred directions of water diffusion exist. More particularly, diffusion along one direction, as selected by the direction of the magnetic field gradient vector could be different than the diffusion along another direction. In the brain, this lack of isotropy of the diffusion coefficient (the so-called "diffusion anisotropy") was, and is, attributed to the presence of nerve fiber tracts along which water is more free to move than it is in directions perpendicular to these tracts.

Accordingly, there is reason to believe that tissue water diffusion cannot be characterized with a single diffusion coefficient D, as for neat liquids. Instead, tissue water diffusion apparently requires a more complex formalism in order to characterize it accurately. This more complex formalism has been found to be presentable using the concept of a diffusion tensor.

A 3×3 matrix may represent the diffusion tensor. This may be accomplished with six independent elements. Indeed, in light of the phenomenon of restricted or anisotropic diffusion, it generally is agreed in the art that at least three directions of the diffusion sensitization gradient (which are independent of the preferred directional diffusion) should be sampled to generate trace images. These trace images are the sum of the diagonal elements of the diffusion tensor. Further, a minimum of 6 directions must be sampled for each voxel, if the full diffusion tensor is to be evaluated for potentially useful studies related to myelination development and brain micro-architecture.

Thus, the current trend in the clinical implementation of diffusion imaging is to sample multiple slices of the brain, each at a low and a high b-factor, the latter being typically on the order of about 1000 sec/mm$^2$. This high b-factor sampling commonly is repeated for at least three, and up to six, directions of the diffusion sensitization gradient. Nevertheless, despite the additional complexity added by the diffusion tensor formalism, the logarithmic plot of signal decay versus b-factor is still seen to follow a substantially mono-exponential best-fit relationship.

Still other experiments, however, have suggested that the mono-exponential signal decay versus b-factor relationship just mentioned may not be necessarily accurate. Thus, studies of cat brain water diffusion have suggested that the signal decay variation with b-factor is a bi-exponential function over a limited b-factor range under 500 sec/mm$^2$. This model, however, has been criticized.

Nevertheless, it appears to be true that the small amplitude, fast diffusing component of the bi-exponential function observed in the very low b-factor range may be attributable to perfusing blood. More specifically, blood in the micro-circulation has a very high diffusion coefficient that is not attributable to the normal, thermal Brownian motion associated with the remainder of the tissue water (i.e., water within and between the cells, but not in the vasculature). Consequently, there is a general consensus that there is indeed a small, very quickly diffusing component contributing to signal decay at low b-factors under 300 sec/mm$^2$ in the brain. Diffusion coefficients determined by signal sampling at different b-factors between 0 and 1000 sec/mm$^2$, therefore, are currently usually referred to as "apparent diffusion coefficients" (ADC), rather than more generically as diffusion coefficients D.

Prior to this invention, routine clinical magnetic resonance diffusion imaging of the brain was conducted at b-factors of between about 100 and 1000 sec/mm$^2$. Average ADC maps then were generated on a pixel-by-pixel basis assuming that the "best-fit" relationship between the magnetic resonance signal and the b-factor is a mono-exponential function (substantially as set forth above with regard to isotropic diffusion).

Still more recently, however, it has been reported that with single volume experiments in rat brains at very high b-factors (up to about 10,000 sec/mm$^2$), the magnetic resonance signal to b-factor relationship also is better explained utilizing a bi-exponential relationship than utilizing a mono-exponential relationship. This suggestion is not as easily dismissed as the blood perfusion case discussed above wherein the overall effect is deemed to be negligible, due to the small blood volume fraction and to be limited to the b-factors under the 300 sec/mm$^2$ range. Hence, if these findings are confirmed, it is expected that the clarity of differentiation of tissue types across an image of a given diffusion weighted magnetic resonance imaged anatomical sample slice may be improved significantly. At the time of the research leading up to the present invention, however, the practical utility of such confirmatory findings remained unclear.

SUMMARY OF THE INVENTION

Accordingly, it is an object of the present invention to provide a water diffusion based, in vivo, magnetic resonance imaging method for the visualization of various tissue pathologies within healthy tissue with greater definition, clarity and speed than has heretofore been possible.

It also is an object of the present invention to provide a method of tissue visualization that provides well-defined, non-invasive imaging without the need for contrast agents with their related complications and cost.

Further, it is an object of the present invention to provide a method of tissue visualization that results in images characterized by very well-defined tissue visualization characteristics using diffusion weighted magnetic resonance imaging on a substantially real-time basis at low cost.

These and other objects and advantages of the present invention arise from the fact that it now has been shown that diffusion-weighted magnetic resonance image signals taken over a wide b-factor range in fact are best described using the bi-exponential model:

$$S(b) = A_1 \exp(-ADC_1 b) + A_2 \exp(-ADC_2 b)$$

This model is derived from the mono-exponential equation discussed above in connection with isotropic diffusion (a concept that will become significant below). In this equation $ADC_1$, and $ADC_2$ are apparent diffusion coefficients, and $A_1$ and $A_2$ are the respective amplitudes thereof. Also, the first term of the equation is known as the "fast" diffusing component, and the second term of the equation is known as the "slow" diffusing component.

This phenomenon is not yet fully understood. It, however, is consistent with a model wherein a pool of water with a very slow diffusion coefficient is located in an exchange relationship with a larger pool having a fast diffusion coefficient. The preferred so-called "wide" b-factor range according to the present invention has been determined to be between about 100 and about 5000 sec/mm².

Therefore, in the preferred embodiment of the method of the present invention, a magnetic resonance imaging apparatus is provided that is capable of performing diffusion-weighted magnetic resonance imaging using b-factors in the range of between about 100 and about 5000 sec/mm². This apparatus is used to generate image data across a selected anatomical slice at b-factors that are commonly equally spaced within the above stated range of b-factors, using at least one gradient direction.

Thus, the data acquired characterizes the diffusion-related signal decays according to a bi-exponential function on a pixel-by-pixel basis. Nevertheless, the method of the invention proceeds to determine the best fit of the diffusion-related decays to a mono-exponential function as discussed above with regard to the prior art. However, this determination is made not because it is believed that the best fit to the acquired data is a mono-exponential function. Instead, it is made to establish a pathologically significant frame of reference for use in association with the following steps of the method.

Thereafter, the $x^2$ (chi²) error parameter associated with mono-exponential fits of the tissue water signal decays with N b-factors is determined according to the following relationship:

$$x^2 = \sum_{l=1}^{N} (S_l - S_o \exp(-ADCb_l))^2$$

This chi²-error parameter constitutes a measure of the departure of the actual average signal decays from the best-fit mono-exponential behavior over the wide b-factor range employed. The amplitudes of these error parameters have been found to provide remarkably well-defined tumor pathology values characterized by extremely high signal-to-noise ratios. Hence, these error parameters then are used to form an image by setting a zero deviation from the mono-exponential behavior to correspond with a black pixel, and causing the brightness of the pixels to increase as the deviation from the predetermined best-fit mono-exponential behavior becomes larger.

Stated slightly differently, it now has been concluded that at least two ADC components are required to describe ADC decay behavior over wide b-factor ranges in adult human brains. This is significant because when the lower b-factor ranges of conventional diffusion-weighted magnetic resonance imaging were used, the best fit achievable to the data points generated was believed to be similar to that characteristic of isotropic diffusion in neat fluids. This, however, was known to be technically incorrect for the reasons discussed above.

The present invention essentially establishes an approximation using a mono-exponential fit of the signal characteristics of water diffusion in tissue measured at each point across the selected slice of brain tissue as a baseline. Then, the chi² error parameter for each corresponding measured data point at each b-factor is determined relative to the so established artificial mono-exponential baseline. Thereafter, the amplitudes of these chi² error parameters are utilized to create the desired image. Of course, the baseline also may be determined using the majority tissue type contained in the imaged slice, for example, white matter. In the latter case, the chi²-error parameter for each measured data point is compared with the chi² error parameter so determined for the predominant tissue type in the imaged slice. This further refines the resultant image so as to delineate even more clearly the location and extent of tissue types different from the predominant tissue type measured across the slice.

This novel approach allows the present invention to provide the desired well defined, non-invasive imaging of tumor pathology without the use of complex and costly paramagnetic contrast agents common to T1-weighted imaging. It also allows each tissue structure to be differentiated from those around it. This is because each section of the resultant image depends upon the characteristic difference of diffusion in and among the cells of the particular tissue type(s) present against the background level of an effectively pure fluid-like diffusion coefficient defined at each point across the entire sample. Thus, there is provided an entirely new concept in the art, a concept that inherently simplifies the computational complexities involved such that desired resultant pathologically significant slice images may be obtained very quickly without the necessity of complex and time consuming data processing.

BRIEF DESCRIPTION OF THE DRAWINGS

These and other objects and advantages of the present invention will be better understood by those skilled in the art in view of the following detailed description of a preferred embodiment of the invention rendered in conjunction with the appended drawings. In the appended drawings, like reference numerals are utilized to refer to like elements throughout, and:

FIG. 7 is a table summarizing our findings of a region of interest analysis for $ADC_1$, $ADC_2$, $A_1$, $A_2$ and chi²/chi² (white matter);

DETAILED DESCRIPTION OF PREFERRED EMBODIMENTS

Figure 1:
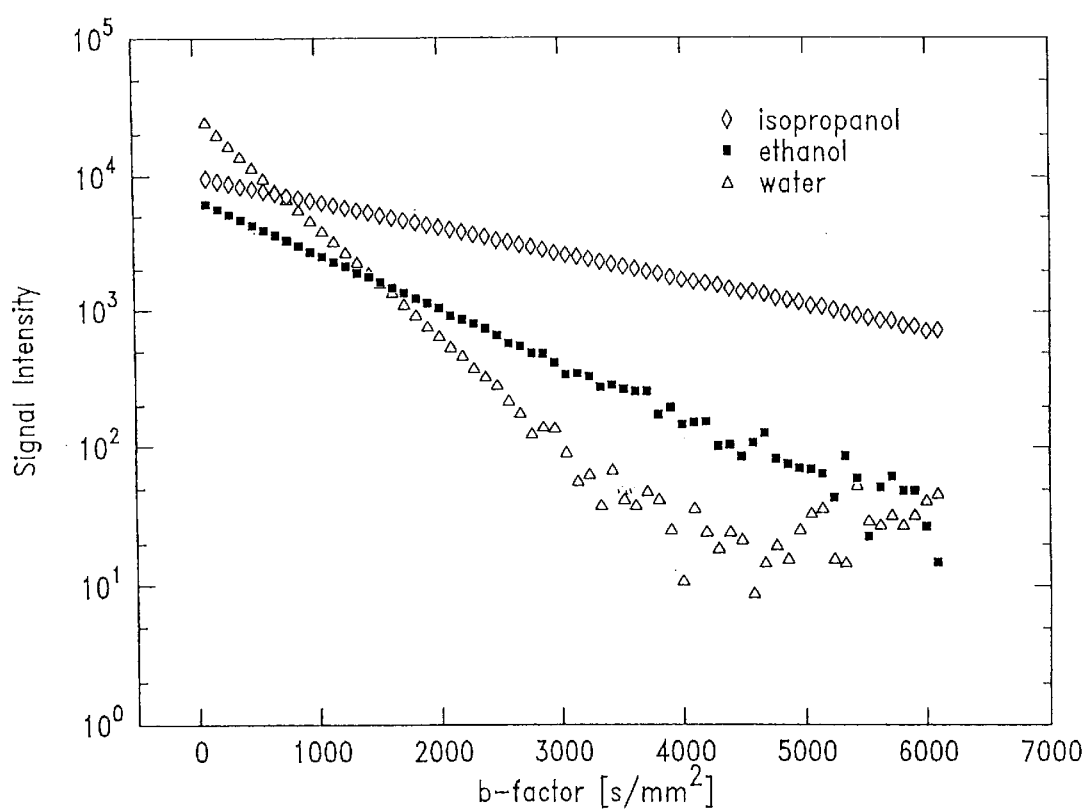
FIG. 1 is an illustrative graphical representation of the logarithmic decay signal intensity from neat solutions of water, ethanol, and isopropanol as a function of b-factor.

As alluded to above, the present invention arises primarily from conceptual inconsistencies that have been recognized in the "best fit" mono-exponential logarithmic plot of magnetic resonance image signal strength vs. b-factor encoding level. Specifically, this plot heretofore has been assumed to exhibit a substantially straight-line characteristic above a threshold noise level both for so-called "isotropic" diffusion, and for so-called "anisotropic" diffusion. This has been true even in view of the signal deviation predicted to arise from blood perfusion. However, it also has been recognized that this is not believed to be a totally technically correct interpretation of the various diffusion phenomena under analysis. Consequently, in cases other than "pure" diffusion, the slope of the logarithmic graphical plot of S vs b mentioned above is referred to as the "apparent diffusion coefficient", rather than the "diffusion coefficient".

Recent brain diffusion studies in rats have suggested that one reason that this inconsistency arises is because the so-called b-factors heretofore used have been limited to the range of between about 100 and 1000 sec/mm². More particularly, these studies suggest that if a higher b-factor range is used, the "best-fit" plot of the magnetic resonance image signal strength S vs. b-factor is a bi-exponential function, rather than a mono-exponential function, at least in rat brains.

If the same phenomena is true in humans, there is a significant potential for the use of diffusion weighted magnetic resonance imaging as a means to differentiate tissue types without the necessity of using complex and costly, paramagnetic contrast agents. It has been found that these contrast agents do not enhance the magnetic resonance signal strength for all tumor types. In addition, paramagnetic contrast agents are not specific to brain tumors, but simply tend to enhance areas where the blood brain barrier has become permeable, for example due to neoplastic growth, inflammation, surgical procedures or radiation therapy. Accordingly, these contrast agents act in a complex manner to enhance the differentiation of atomic level spins in the different tissue types. However, these contrast agents also can add complexity to, or even ruin, the image analyses they are intended to enhance.

It now has been determined in humans that by using b-factors in a range some five times larger than the range currently clinically prevalent (i.e., between about 100 and 5000 sec/mm², instead of between about 0 and 1000 sec/mm²), similar results to the above-referred-to research in rats occur. Therefore, the "best-fit" bi-exponential model of S vs. b is more accurate than the previously adopted mono-exponential model. The ramifications of this are significant as will be discussed in greater detail in the example below.

The various steps of the method of the invention now will be discussed. These steps include:

(1) the provision of an appropriate magnetic resonance imaging apparatus;

(2) acquiring a plurality of sets of signal decays from a patient using the magnetic resonance imaging apparatus at each of a selected number of encoding levels distributed across a wide range of b-factors;

(3) processing the acquired signal decays on a pixel by pixel basis to obtain the best possible fit between them and a mono-exponential equation of the form:

$$S = S_0 \exp(-bD)$$

In this equation, $S_0$ is a constant that depends on constant values associated with (a) the magnetic imaging apparatus, (b) the spin-spin relaxation time T2, (c) the spin-lattice relaxation time T1, and (d) the spin density ρ. Also, b is the diffusion encoding level, and D is the diffusion coefficient representing the slope of the natural logarithm of S vs b;

(4) determining the $chi^2$ error between the best fit mono-exponential equation and the measured signal decay for each pixel; and (5) displaying the $chi^2$ errors so determined as the amplitudes of a resultant image such that an error of zero is displayed as a black pixel, and larger errors are assigned a brightness value according to the magnitude of the error involved.

The line scan diffusion imaging technique appears to be suitable for obtaining motion artifact free images even at very high b-factors of up to 5000 sec/mm². The fact that in one study very high diffusion weighting failed in only one out of fifteen patients is evidence for the remarkable degree of robustness of this technique. It is believed, however, that other imaging techniques such as single-shot diffusion weighted echo-planar imaging (EPI) (see, Turner R, Le Bihan D, Maier J, Vavrek R, Hedges LK, and Pekar J.; Echo-Planar Imaging of Intravoxel Incoherent Motions, *Radiology*, 177:407–414, 1990) would be equally insensitive to motion. In addition, with EPI, data from more than one slice could be obtained without increasing scan time. Nevertheless, EPI has been shown to be susceptible to ghosting artifacts and image distortion, among other problems. Line scan diffusion imaging, on the other hand, has been found not to be susceptible to these artifacts, even at high b-factors.

In view of this, the preferred embodiment of the invention herein described illustratively adopts the line scan imaging technique. This technique and an apparatus suitable for the practice thereof is described in detail in U.S. Pat. No. 5,786,692 issued on Jul. 28, 1998 to Stephan E. Maier, et al. and entitled "Line Scan Diffusion Imaging", which is hereby incorporated by reference into this specification.

Figure 2:
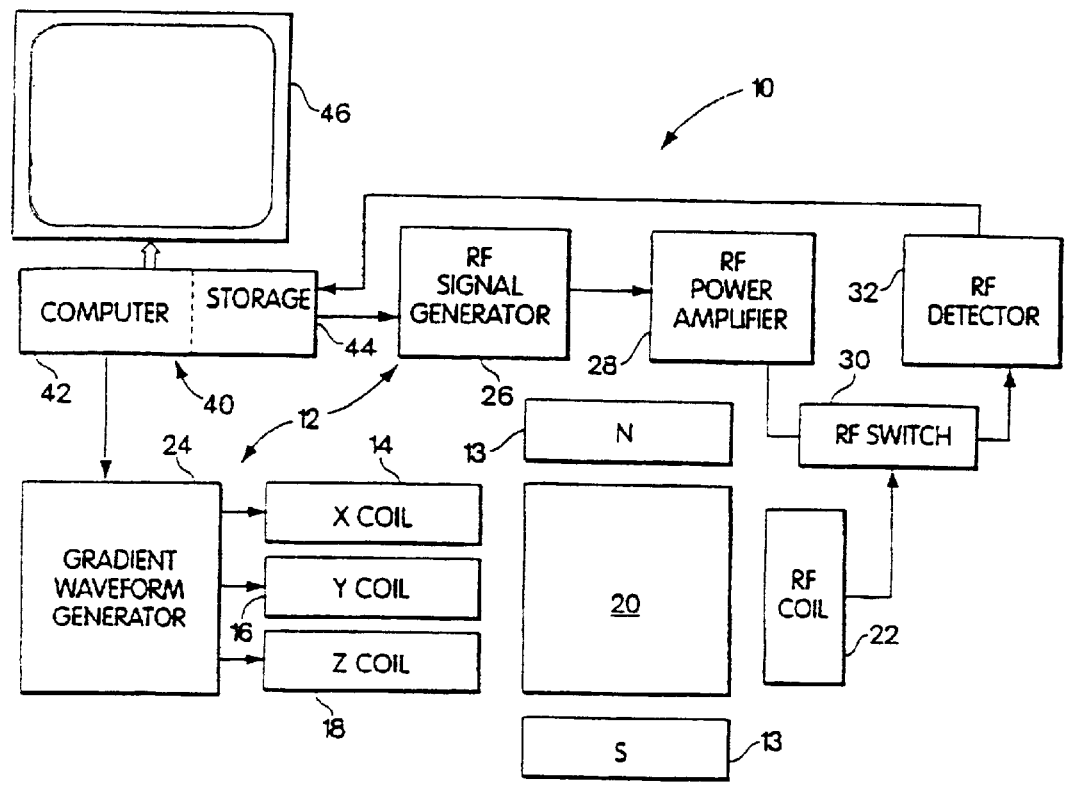
FIG. 2 is a high-level block diagram of an illustrative embodiment of a magnetic imaging system suitable for use in the method of the present invention.
Figure 3:
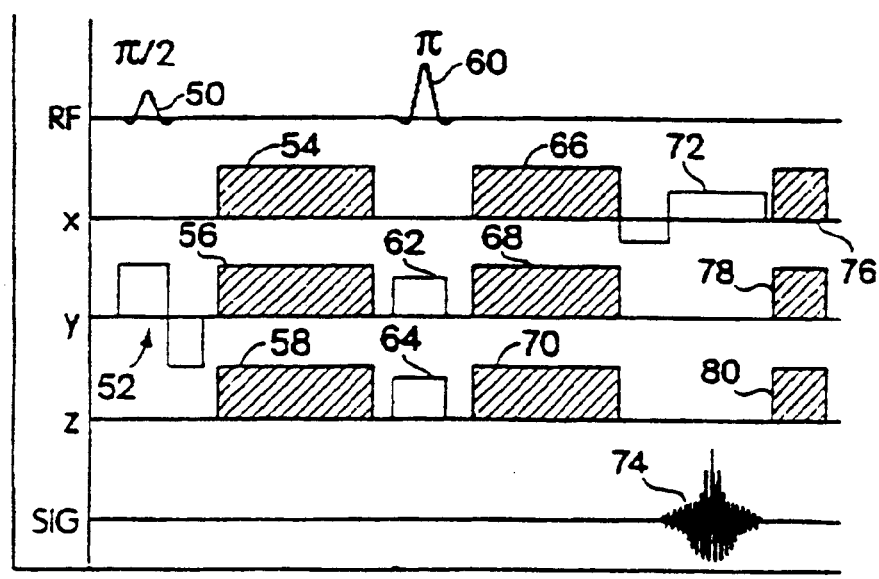
FIG. 3 is an imaging sequence diagram for the acquisition of one line of data from one column using the system illustratively depicted in FIG. 2.

In summary, however, as will be seen from FIGS. 2 and 3, this apparatus includes an illustrative magnetic resonance imaging system 10, generally having a magnet assembly, interface circuitry, and a computer 40. The magnet assembly includes a very strong magnet 13 that creates a homogenous magnetic field within and around a sample (e.g. an inert sample or patient). X, Y, and Z magnetic field gradient coils 14, 16 and 18 also form a part of the assembly and are positioned proximate or surrounding the sample 20. The assembly further comprises one or more RF coils 22, which are positioned near or around the sample.

The interface circuitry includes a gradient waveform generator 24 that has signal outputs connected to the gradient coils 14, 16 and 18, and a control input connected to the computer. An RF signal generator 26 also has a control input connected to the computer and an output connected to an input of an RF power amplifier 28. The RF power amplifier has an output connected to an input of an RF switch 30. The RF switch is connected to the RF coil 22, and has an output connected to the input of an RF detector 32.

The computer 40 includes computing hardware 42 and storage 44. The computing hardware can comprise special purpose hard-wired computing circuitry dedicated to MR acquisition, an imaging and a special programmed general-purpose computer, or a combination of both. The storage 46 can include various types of storage, such as disk storage and random access memory.

The storage can be used to store data and programs, including the programs used to interact with the system's interface circuitry 12. The computer has a video output for providing video signals to display 46, as well as control outputs connected respectively to control inputs of the gradient waveform generator 24 and the RF signal generator 26. The computer also has acquisition input operatively connected to an output of the RF detector 32.

In operation, referring to FIGS. 2 and 3, the imaging system 10 builds an image on a line-by-line basis under control of the computer 40 according to a line scan diffusion imaging (LSDI) sequence. At the beginning of an acquisition sequence for a line, the computer 44 sends a signal to the RF signal generator 26, which responds by generating a $\pi/2$ pulse 50. This pulse is amplified by the RF power amplifier 28 and provided to the RF coil 22 via the RF switch 30. As this pulse is being provided, the computer instructs the gradient waveform generator 24 to drive the Y coil 16 with a slice selective bipolar pulse 52.

Next, the gradient waveform generator 24 provides a first set of diffusion gradient pulses 54, 56, and 58 respectively to the X, Y, and Z gradient coils 14, 16 and 18. These gradient signals each include a signal rectangular pulse, which is provided in order to sensitize the MR imaging process to diffusion. After the falling edge of the diffusion gradient signals, a $\pi$ pulse 60 is provided to the RF coil 22 in much the same way that the $\pi/2$ pulse was. At the same time, the gradient waveform generator provides a rectangular pulse on each of the Y and Z gradient coils (pulses 62, 64). These pulses are of lower amplitude and shorter duration than the diffusion gradient pulses. Then, the waveform generator provides a second set of diffusion gradient signals 66, 68 and 70 respectively to the X, Y and Z gradient coils 14, 16 and 18. These second diffusion gradient signals are of the same amplitude and duration as the first diffusion gradient signals. Once the second diffusion gradient signals are turned off, the gradient waveform generator provides a readout pulse 72 on the X coil 14.

As a result of this excitation sequence, an echo 74 is received from the intersection of the slices defined by the $\pi/2$ and $\pi$ pulses. The RF coil receives this echo and provides it via the RF switch 30 to the RF detector 32. The computer 40 receives the output of the detector, and processes it to obtain one line to be displayed on the display 46. After the echo has been received, optional crusher gradient signals 76, 78, and 80 can be applied to the gradient coils 14, 16 and 18.

The method then proceeds with the acquisition of a set of signal decays from a patient using the magnetic resonance imaging apparatus at each of a selected plurality of encoding levels distributed across the range of b-factors within its capability. This is accomplished by varying the gradient amplitude G in the equation for the b-factor: $b=\gamma^2 G^2 \delta^2(\Delta-\delta/3)$. Each of the acquired sets of signal decays is representative of an image of a selected anatomical cross-section of the patient. Further, each individual signal decay in each set corresponds to a pixel of its associated image.

Thereafter, the acquired signal decays are processed on a pixel by pixel basis to obtain the best possible fit between them and a mono-exponential equation of the form:

$$S=S_0 \exp(-bD).$$

In this equation $S_0$ is a constant that depends (1) on constant values associated with the magnetic imaging apparatus, (2) the spin-spin relaxation time T2, (3) the spin-lattice relaxation time T1, and (4) the spin density $\rho$. Also in this equation, b is the diffusion encoding level, and D is the diffusion coefficient representing the slope of the logarithm of S vs b. Preferably, the best possible fit is obtained with an advanced method such as the Levenberg-Marquardt algorithm.

The chi$^2$-error between this best fit and the measured signal decay for each pixel is then determined.

Finally, the chi$^2$-errors so determined are displayed as the amplitudes of a resultant image such that an error of zero is displayed as black pixel, and the larger the error is the brighter the display of the associated pixels becomes.

The following example will further describe the invention in terms of the actual experimental process, which led to its creation.

EXAMPLE

With wide b-factor range diffusion scans along a single column it has been demonstrated that human brain water attenuation is better described with a bi-exponential model than a mono-exponential model as previously believed. Thus, data in image formats was obtained with line scan diffusion imaging (LSDI). Specifically, 15 brain tumor scans were performed on patients. One patient was studied both before and after contrast agent administration. Altogether, four examinations were carried out before contrast administration. The data relating to one patient had to be discarded because of motion artifacts. The pathologies of the remaining 13 patients included 8 glioblastoma multiforme, 2 astrocytomas and 3 metastases. In addition, one normal patient and one stoke patient two days after the onset of symptoms also were scanned.

A wide range b-factor LSDI sequence and protocol was implemented on a 1.5 Tesla Horizon Echospeed (GE Medical Systems, Milwaukee, Wis.) system with software release 5.7. Sixteen images with evenly spaced b-factors ranging from 5 to 5000 sec/mm$^2$ were acquired. A maximum gradient amplitude of 22 mT/m along each magnet main axis and the concurrent use of all three gradient directions permitted a minimum echo time of 94 ms. For normal subjects, data for six diffusion directions was collected. Following the diffusion tensor formalism, a geometric average of the signals was formed by multiplying all six signal values and taking the sixth root of the multiplied value. For patients, data was collected for one diffusion direction only. Images were obtained at a rectangular field of view of 220×165 mm$^2$ and a matrix size of 64×48 columns. The effective section thickness was set at 7.3 mm. The bandwidth was +/–4 kHz. TR and effective TR were 204 and 2040 ms, respectively. A considerably shorter TR, while technically possible, was not selected because of gradient heating concerns. A total scan time for a single slice location and one diffusion direction was 3 minutes. Neither cardiac gating nor head restraints were employed.

Figure 4:
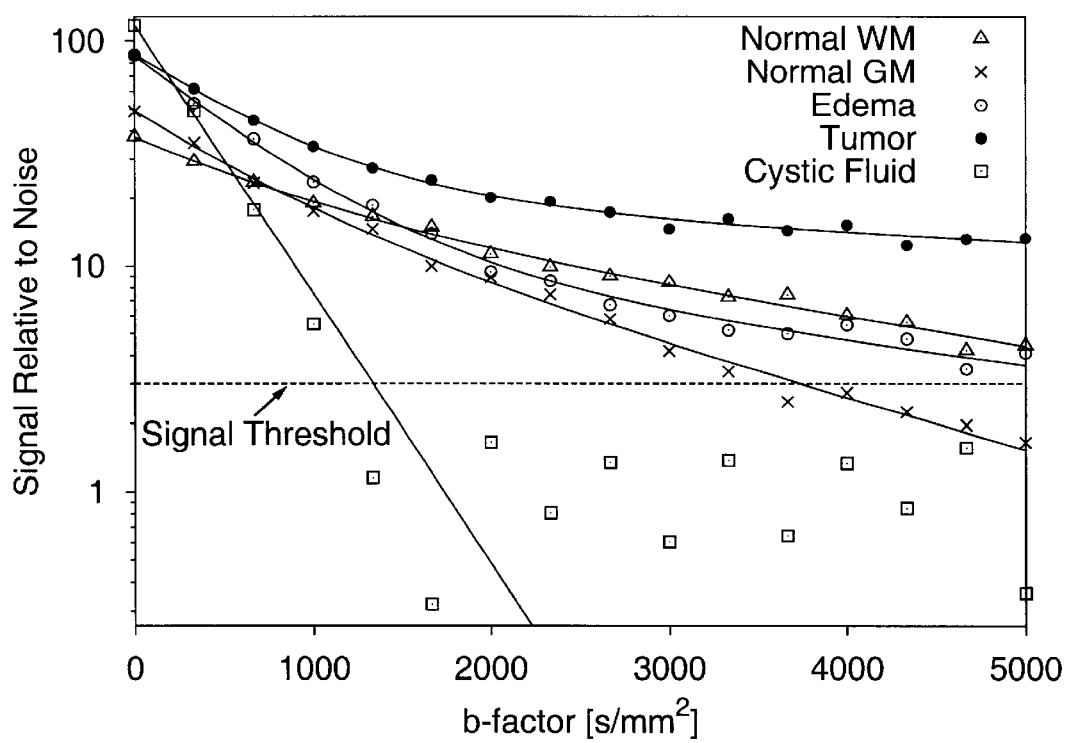
FIG. 4 is a logarithmic plot of various signal intensities vs b-factor for several tissue types.

FIG. 4 shows an example logarithmic plot of signal intensities vs. b-factor for individual pixels in areas of white matter (WM), gray matter (GM), edema, tumor, and cystic fluid. Only by grossly exceeding the normal clinically used b-factor range of 0 to 1000 sec/mm$^2$, does the bi-exponential nature of the signal decay for white matter, gray matter, edema, and tumor become apparent (Note: if the decay was mono-exponential, the signal decay on the logarithmic plot would follow a straight line). Noise cannot explain this bi-exponential decay since, except for cystic fluid, up to a b-factor of 5000 sec/mm$^2$ all signals are above the noise threshold. The noise threshold can be appreciated from the cystic fluid signal, which reaches the noise level at a b-factor of approximately 1500 sec/mm$^2$.

Image reconstruction was performed with standard scanner software. Bi-exponential and mono-exponential fitting using the Levenberg-Marquardt algorithm was performed off line. A C-program performing the bi-exponential calculations only on points within the skull, required several minutes of computation time, when running on an Intel 667

MHz PC with a Linux Operating System, version 2.2.13. It appeared that due to noise in the signal decays, bi-exponential values were completely falsely estimated in some points of the images, which resulted in images of the fit parameter with speckles in areas one could assume should have been uniform in appearance. These speckles, of course, could clearly limit the diagnostic value of such images. For each slice, regions of interest (ROI) were drawn and analyzed for normal white matter (WM), normal gray matter (GM), edematous and tumor/stroke tissue, and cysts, respectively. This is shown in FIGS. 5A to 5D.

Figure 5A:
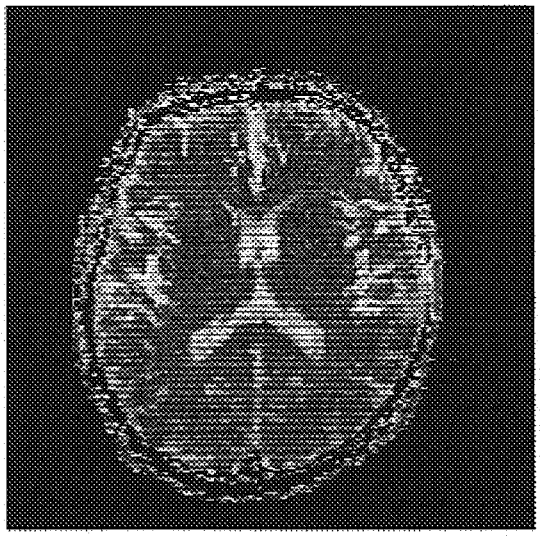
FIGS. 5A–5D are illustrative images generated from a bi-exponential analysis of a wide b-factor range obtained from a normal subject.
Figure 5B:
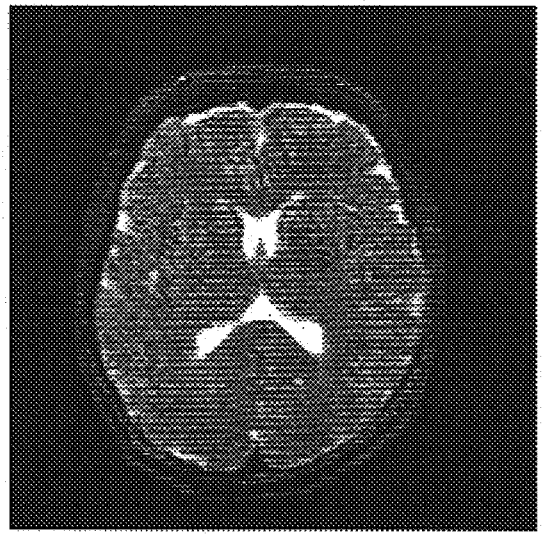
Figure 5C:
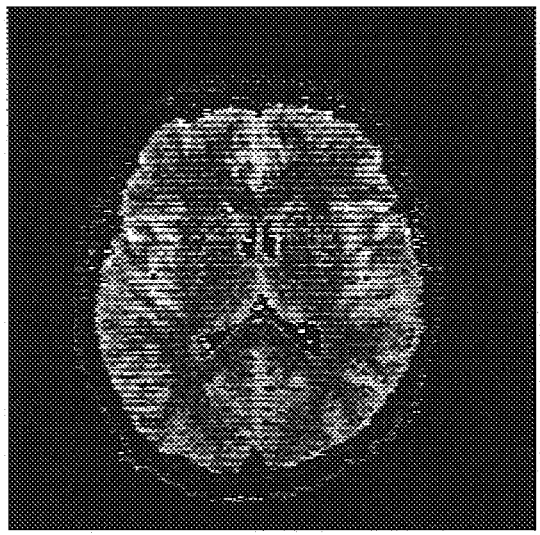
Figure 5D:
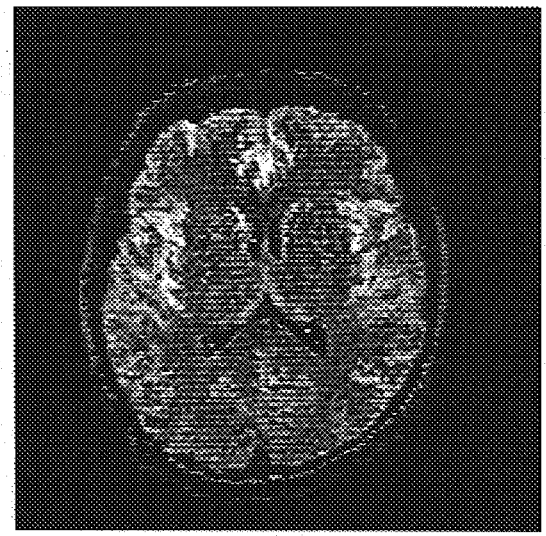

Specifically, FIGS. 5A to 5D (FIG. 5A: $ADC_1$; FIG. 5B: $A_1$; FIG. 5C: $ADC_2$; and FIG. 5D: $A_2$) images generated from the bi-exponential analysis of wide-range diffusion data obtained for a normal subject. Data of six diffusion-weighting directions (tensor configuration [6]) were averaged to eliminate effects of anisotropic diffusion. On the $ADC_2$ and $A_2$ maps, values within the ventricles are zero, since the signal decay in cerebro-spinal fluid (CSF) is mono-exponential. Moreover, on the maps of the slow diffusing component, white and gray matter appear to have different values.

T2-weighted images and post contrast T1-weighted images were used to locate edema and tumor. Further, to avoid the influence of directional diffusion in normal white matter, the average value of two independent and rather large white matter ROI's were used to assess white matter values.

Figure 6:
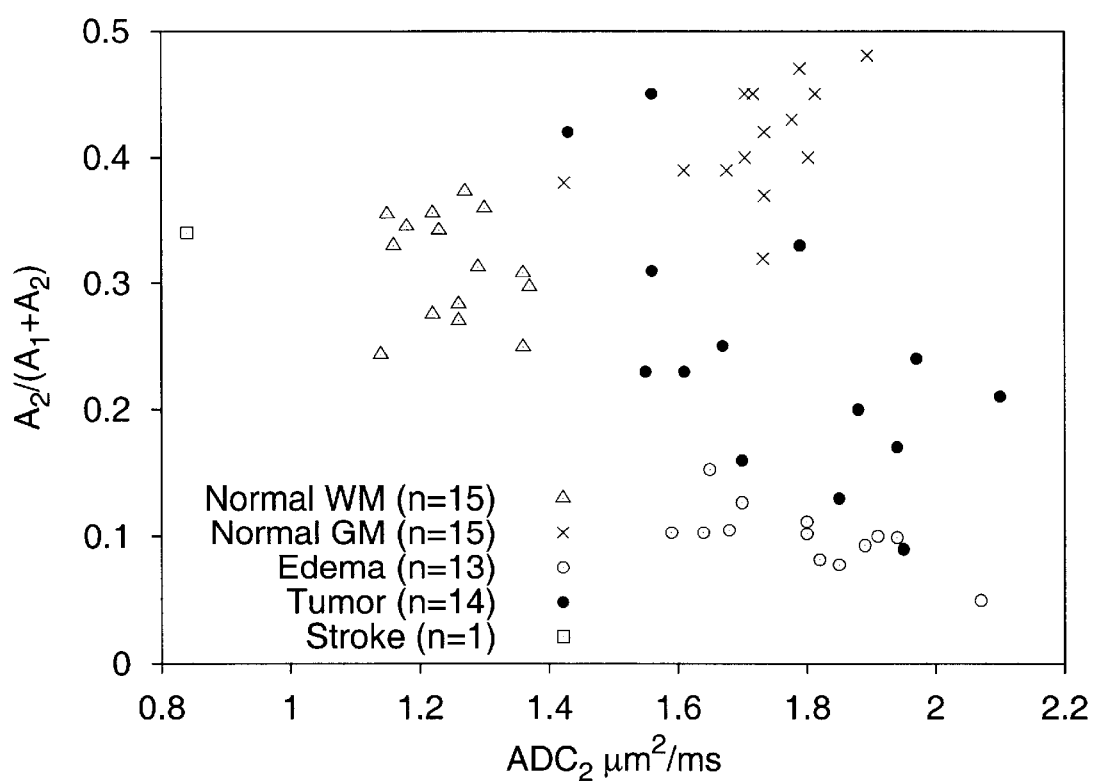
FIG. 6 is an illustrative scatter plot of the relative $A_2$ amplitude versus the fast diffusion coefficient $ADC_1$ measured in individual regions of interest.
Figure 8A:
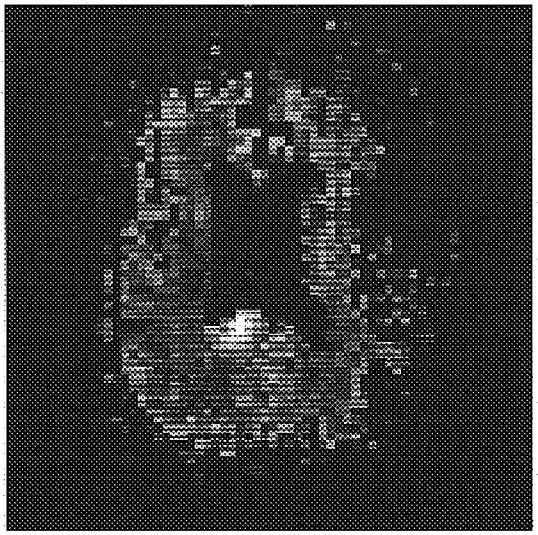
FIGS. 8A to 8C together constitute an illustrative comparison of a pre-contrast $A_2$ image with bright tumor lesion with conventional T1 and T2-weighted images.
Figure 8B:
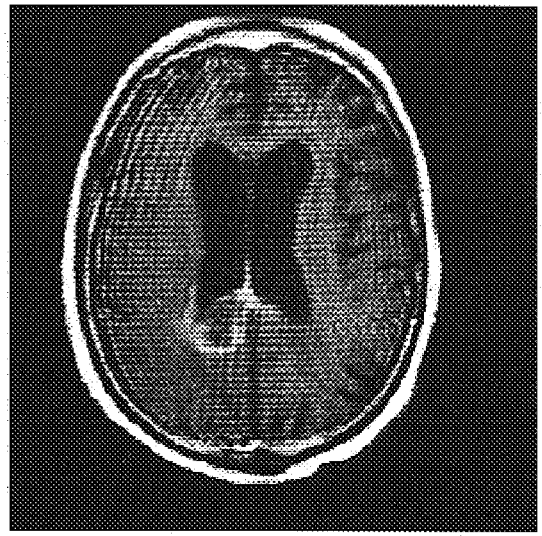
Figure 8C:
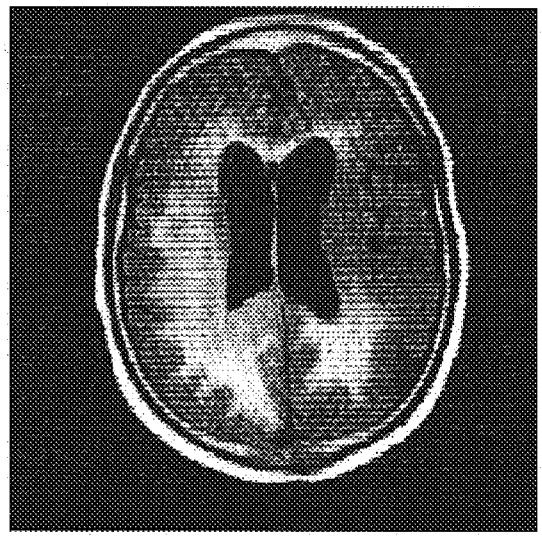

FIG. 6 shows a scatter plot of the amplitude fraction $A_2/(A_1+A_2)$ versus the first diffusion constant $ADC_1$ measured in the individual regions of interest. The table shown in FIG. 7 summarizes the findings of region of interest analysis for $ADC_1$, $ADC_2$, and their respective amplitudes $A_1$ and $A_2$. Standard deviations are given in parentheses. Bi-exponential fits were required for all tissues. The fast diffusing component $ADC_1$ of edematous and tumor tissue was found to be considerably higher than in normal white matter, whereas the slow diffusing component did not differ significantly. For cystic fluid, the best fit was mono-exponential with a very high ADC value. Further, as expected, $ADC_1$ and $ADC_2$ for stroke were lower than the values for normal white matter. The amplitudes $A_1$ and $A_2$ of all tissues differed considerably. In comparison to $A_1$ of white matter, both edematous and tumorous $A_1$ were strongly elevated. Similarly, however, with a notable large standard deviation, $A_2$ in tumorous tissue was higher. This is shown in FIGS. 8A to 8C wherein a pre-contrast $A_2$ image (FIG. 8A) with a bright tumor lesion and conventional T1 (FIG. 8B) and T2-(FIG. 8C) weighted images are depicted. Here the T1-weighted post-contrast image shows the contrast enhanced tumor margin. Further, the extent of edema can be seen on the T2-weighted image with a FLAIR suppressed CSF signal. On the other hand, a reduced $A_2$ was observed in edematous tissue.

The effect of perfusion also was considered. To eliminate the blood signal influence at very low b-values, bi-exponential fitting without the first value, i.e., with b-values between 338 and 5000 sec/mm² only, was performed. Region of interest analysis of this second data set produced values that differed only a few percent from the results that included the lowest b-value. Moreover, the effect of signal-to-noise ratio was verified by fitting region of interest signals instead of individual pixels. This approach did not reveal any noteworthy differences.

It is believed that the use of a higher peak gradient in the area of about 40 mT/m and an increase in maximum gradient duty cycle will permit at least a 50% reduction in scan time. Furthermore, single-shot techniques that employ phase encoding, such as echo-planar or slab-scan imaging, will allow several slices to be measured within the same scan time. Hence, it does not seem to be unrealistic to expect that multi-directional and multi-b-factor coverage of the brain with a scan time on the order of five minutes will soon be possible. Nevertheless, the calculation of bi-exponential fits is computationally demanding, time consuming, and error prone for low signal-to-noise ratios, as specifically noted above. This is true even when the required calculations are accomplished by the use of very high speed computers. Hence, while the parameters of the bi-exponential equation $A_1$, $A_2$, $ADC_1$, and $ADC_2$, all provide image data useful in tissue differentiation, the time and expense associated with the acquisition thereof is almost prohibitive.

In light of this, it was recalled that during the course of the original analysis of the bi-exponential parameters it had been realized that variations in the amplitudes of the ADC components due to RF coil inhomogeneities are relatively small within the skull. Accordingly, the relationships $A_1/A_1$ (WM) and $A_2/A_2$ (WM) were both found to be significant in the demarcation of various tissue types (see FIGS. 5A to 5D). Accordingly, what was needed was a way of quickly and inexpensively analyzing the data that had been demonstrated to display a best fit to a bi-exponential model.

The answer to this problem was found in the realization that heretofore for b-factors in the normal clinical range of up to about 1000 sec/mm² it had been believed that a mono-exponential model best represented the ADC value. That mono-exponential model was known to be in error for various reasons, and also was known to accurately characterize diffusion in fluids. From this, it was postulated that a relationship that would quantify the difference between measured signal amplitudes and a fit abstractly representative of the diffusion coefficient of the anatomical structure of interest would also be indicative of differing tissue types. The relationship that currently appears to best fit these criteria is the so-called "chi²" error parameter.

Figure 9A:
FIGS. 9A to 9D are illustrative comparisons of chi²-error (FIGS. 9A and 9C) and contrast-enhanced T1-weighted (FIGS. 9B and 9D) images of two brain tumor patients.
Figure 9B:
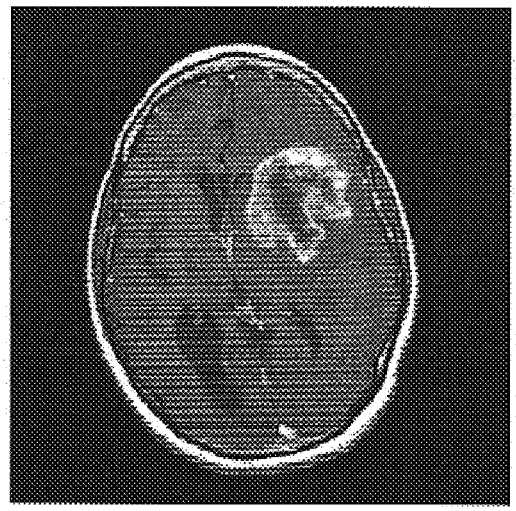
Figure 9C:
Figure 9D:
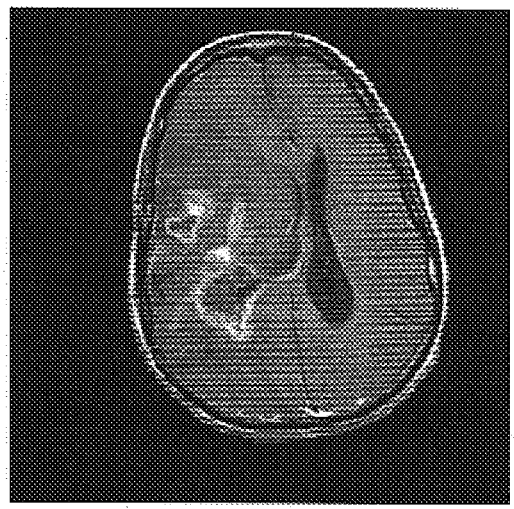

Accordingly, the same regions of interest as had been used for the multi-component ADC analysis were used to determine the average chi² values of white matter, tumor, edema, and cystic fluid relative to the mono-exponential ADC fit curve for the same data. As can be seen from the table shown in FIG. 7 and the images shown in FIGS. 9A and 9C, in comparison to white matter chi² values, chi² in edema and particularly tumor is strongly elevated, whereas in cysts chi² is greatly reduced. Chi²-error images (i.e., images of the amplitude of the deviation of a measured signal value from the analysis baseline) provided excellent visualization of tumor tissue in 10 out of the 14 scans. The average ratio between chi² of tumor and normal white matter in those 10 cases was 5.36+/−2.45. The two image examples depicted in FIGS. 9A and 9C provide proof of the excellent contrast between tumor and surrounding tissue. Tissue enhancement was also evident on the images obtained at the highest diffusion weightings, but, the contrast between tumor and surrounding tissue was considerably smaller than observed with the chi² derived images.

Further, and perhaps most importantly, the chi² images display a high signal-to-noise ratio arising from the fact that they are calculated based upon the sum of the chi² values from each voxel of interest measured at several b-factors. This also permits high-resolution matrices of about 128×96 pixels to be utilized. In addition, the computation of chi² images is not computationally demanding, and in fact can be performed almost instantly on very basic computer equipment such as the scanner computer console (see for example FIG. 2). Therefore, highly pathologically informative $chi^2$ images can be almost immediately available.

Having thus described a preferred embodiment of the invention and an example indicative of its significance in the art, numerous modifications, alterations, variations, changes and the like will occur to those skilled in the art. For example, various ways of quantifying the difference between measured signal amplitudes and a curve abstractly representative of the mono-exponential isotropic diffusion coefficient within the anatomical structure of interest may occur to those skilled in the art within the scope of this invention in its broadest aspects. Included among these are forms of the $chi^2$-error parameter such as its square root, functions of the $chi^2$-error parameter that vary proportionally therewith, and other alternatives. Accordingly, it is to be understood that the foregoing specification is to be understood as being illustrative only, and the scope of the invention is intended to be limited only by the terms of the appended claims.

What is claimed is:

1. A method for very fast, in vivo, differential tissue characterization, said method comprising the steps of:
    a) providing a magnetic resonance imaging apparatus capable of operation at diffusion encoding levels (b-factors) at least between about 100 sec/mm$^2$ and about 5000 sec/mm$^2$;
    b) acquiring a set of signal decays from a patient using said magnetic resonance imaging apparatus at each of a selected plurality of encoding levels distributed across the range of b-factors within its capability, each said set of signal decays being representative of an image of a preselected anatomical cross-section of the patient, and each said signal decay of each said set corresponding to a pixel of its associated image;
    c) processing said acquired signal decays on a pixel by pixel basis to obtain the best possible fit between them and the mono-exponential equation:

$$S = S_0 \exp(-bD)$$

wherein $S_0$ is a constant that depends on (i) constant values associated with the magnetic imaging apparatus, (ii) the spin-spin relaxation time T2, (iii) the spin-lattice relaxation time T1, and (iv) the spin density $\rho$, wherein b is the diffusion encoding level, and wherein D is the diffusion coefficient representing the slope of the natural logarithm of S vs b;

d) quantifying the differences between the best fit determined in step c and the measured signal decay for each pixel; and e) displaying the quantified differences determined in step d as the amplitudes of a resultant image such that a difference of zero is displayed as a black pixel, and the larger the difference is the brighter the display of the associated pixel becomes.

2. The method according to claim 1, wherein step (d) is accomplished by determining the $chi^2$-error between the best fit determined in step (c) and the measured signal decay for each pixel.

3. The method according to claim 2, further comprising the steps of:
    (i) determining the $chi^2$-error for the best fit determined in step c with those measured signal decays associated with the type of tissue most prevalent within the imaged slice; and
    (ii) displaying the $chi^2$-errors determined in step d relative to the $chi^2$ errors determined in the last stated step.

4. The method according to claim 1, wherein step (d) is accomplished by determining the square root of the $chi^2$-error between the best fit determined in step (c) and the average measured signal decay for each pixel.

5. The method according to claim 1, wherein step (d) is accomplished by determining the value of a function that varies proportionally with the $chi^2$-error between the best fit determined in step (c) and the measured signal decay for each pixel.

* * * * *